US011988633B2

United States Patent
Limjap et al.

(10) Patent No.: US 11,988,633 B2
(45) Date of Patent: May 21, 2024

(54) USE OF POLYAMINES AS RESOLVING AGENTS FOR CAPILLARY ELECTROPHORESIS OF LABELED GLYCANS USING GELS

(71) Applicant: Agilent Technologies, Inc., Santa Clara, CA (US)

(72) Inventors: Fielito U. Limjap, Newark, CA (US); Michael J. Kimzey, Oakland, CA (US); Francis T. Haxo, San Francisco, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 695 days.

(21) Appl. No.: 16/644,467

(22) PCT Filed: Sep. 20, 2018

(86) PCT No.: PCT/US2018/052079
§ 371 (c)(1),
(2) Date: Mar. 4, 2020

(87) PCT Pub. No.: WO2019/060633
PCT Pub. Date: Mar. 28, 2019

(65) Prior Publication Data
US 2021/0063347 A1    Mar. 4, 2021

Related U.S. Application Data

(60) Provisional application No. 62/562,189, filed on Sep. 22, 2017.

(51) Int. Cl.
*G01N 27/447* (2006.01)
*C08B 37/00* (2006.01)
(Continued)

(52) U.S. Cl.
CPC ... *G01N 27/44747* (2013.01); *C08B 37/0003* (2013.01); *C08B 37/0087* (2013.01);
(Continued)

(58) Field of Classification Search
CPC ........ G01N 27/44747; G01N 27/44791; C08L 79/02
See application file for complete search history.

(56) References Cited

U.S. PATENT DOCUMENTS 4,865,707 A    9/1989  Karger
4,911,807 A *  3/1990  Burd ................ G01N 27/44717
                                                      204/453
(Continued)

FOREIGN PATENT DOCUMENTS

WO    WO 93/15394           8/1993
WO    WO 93/015394 A1       8/1993
WO    WO 1997/004308 A1     2/1997

OTHER PUBLICATIONS

Temed C6H16N2 PubChem (Year: 2022).*
(Continued)

*Primary Examiner* — Caitlyn Mingyun Sun
(74) *Attorney, Agent, or Firm* — Laurence J. Hyman; Hyman IP Law (57) ABSTRACT

The present disclosure provides methods of improving the resolution of labeled glycans in capillary electrophoresis techniques using a gel as a sieving matrix, by incorporating polyamines in the gel.

20 Claims, 2 Drawing Sheets

(51) Int. Cl.
  *C08G 73/02* (2006.01)
  *C08L 79/02* (2006.01)
(52) U.S. Cl.
  CPC ..... *C08G 73/0206* (2013.01); *C08G 73/0273* (2013.01); *C08L 79/02* (2013.01); *G01N 27/44791* (2013.01)

(56) References Cited

U.S. PATENT DOCUMENTS

| | | | | |
|---|---|---|---|---|
| 5,114,550 | A * | 5/1992 | Schomburg | B01D 57/02 204/605 |
| 5,277,780 | A | 1/1994 | Kambara | |
| 5,302,264 | A * | 4/1994 | Welch | G01N 27/44704 204/601 |
| 5,798,032 | A | 8/1998 | Khan | |
| 6,083,372 | A * | 7/2000 | Grover | G01N 27/44752 204/601 |
| 9,222,913 | B2 | 12/2015 | Deschamps | |
| 2004/0094481 | A1 | 5/2004 | Que | |
| 2005/0053944 | A1 * | 3/2005 | Fuchs | G01N 27/44726 435/6.12 |
| 2011/0031120 | A1 | 2/2011 | Inche | |
| 2011/0104661 | A1 * | 5/2011 | Kwon | C08L 33/26 204/461 |
| 2017/0045538 | A1 * | 2/2017 | Guttman | G01N 35/0099 |

OTHER PUBLICATIONS

Y. Xu, The Chemical Education, Tutorial: Capillary Electrophoresis, 1996, 1(2), p. 1-14. (Year: 1996).*

Hamm, et al., Characterization of N-Linked Glycosylation in a Monoclonal Antibody Produced in NS0 Cells Using Capillary . . . , Pharmaceuticals, 2013, pp. 293-406. vol. 6.

Kimzey et al., "Gly-Q: An Integrated Solution for High-throughput, User-friendly Glycoanalysis Using Rapid Separation for Capillary . . . " ProZyme, 2004, p. 1-4 d.

Young, Lee W., International Search Report. International Application PCT/US2018/052079, issued Dec. 21, 2018.

Young, Lee W., Written Opinion, International Application PCT/US2018/052079, issued Dec. 21, 2018.

Michalitsch, Richard, Extended European Search Report for EP Appln. 18857998.1, May 21, 2021, EPO, Munich, Germany.

* cited by examiner

USE OF POLYAMINES AS RESOLVING AGENTS FOR CAPILLARY ELECTROPHORESIS OF LABELED GLYCANS USING GELS

CROSS-REFERENCE TO RELATED APPLICATIONS

This is a national stage application under 35 U.S.C. § 371 of International Application No. PCT/US2018/052079, filed Sep. 20, 2018, which is hereby incorporated by reference for all purposes. This application further claims priority to U.S. Provisional Patent Application No. 62/562,189, filed Sep. 22, 2017, the contents of which are incorporated herein for all purposes.

STATEMENT OF FEDERAL FUNDING

Not applicable.

BACKGROUND OF THE INVENTION

This invention relates to the field of analysis of glycans.

Many of the proteins produced by eukaryotic cells are modified after translation by the addition of covalently-linked, linear or branched chains of carbohydrates. These protein-carbohydrate conjugates are referred to as glycoproteins; the point at which the carbohydrate is attached is referred to as a glycosylation site. Attached polysaccharides or oligosaccharides are referred to as glycans. A wide range of glycans are found on the different glycosylation sites of particular glycoproteins. The particular pattern of glycans on a particular glycoprotein is determined by the specific cell line that produced the protein and the conditions under which the cells were grown.

Since the glycans conjugated to a protein can affect characteristics critical to its function, including pharmacokinetics, stability, bioactivity, or immunogenicity, it is important in many uses to determine which glycans are present. For example, the Food and Drug Administration requires characterization of carbohydrates attached to biologics (such as therapeutic glycoproteins and vaccines) to show composition of matter and consistency of manufacture, resulting in a need for extensive characterization of the product. Analysis of the profile of the released carbohydrates is also important for quality control in the production of recombinant proteins, in which a change in carbohydrate profile may indicate stress in the system, signaling conditions that may require a commercial-scale fermenter of expensive protein to be discarded.

Glycans released from glycoconjugates are typically treated to label their free-reducing terminus with a fluorescent dye or other detectable moiety, and the labeled glycans are then analyzed by methods such as high performance liquid chromatography (HPLC), capillary electrophoresis (CE), or carbohydrate gel electrophoresis.

One problem that has plagued the identification of labeled glycans by CE has been differentiating glycans that co-migrate with each other. Hindering co-migration of labeled glycans would improve resolution of the glycans present in the sample being analyzed. Unfortunately, to date, compositions and methods for reducing co-migration of labeled glycans, and thus for improving resolution, have not been reported.

U.S. Pat. No. 9,222,913 teaches the use of certain polyamines to reduce electro-osmotic flux in separating hemoglobin molecules (glycated protein chains in which sugars are non-enzymatically attached to the N-terminus or to a lesser extent to lysine residues).

There remains a need for compositions and methods that improve resolution of labeled glycans that co-migrate together during CE. Surprisingly, the present invention meets these and other needs.

SUMMARY

The invention provides methods, compositions, and kits for improving the separation of labeled glycans in a sample by capillary electrophoresis analysis, wherein the separation takes place in a gel, wherein the gel comprises a polyamine having a structure of any of Structure 1 wherein $R_1$, $R_2$, and $R_3$ are independently selected from H and $CH_3$, Structure 2 wherein each $R_1$ and each $R_2$ is independently selected from H and $CH_3$, Structure 3 wherein each of $R_1$ and $R_2$ are independently selected from H and $CH_3$,

Structure 4 wherein each of $R_1$-$R_3$ is independently selected from H and $CH_3$, Structure 5 wherein each of $R_1$-$R_4$ can independently be H or $CH_3$,
Structure 6, wherein each of $R_1$-$R_6$ can independently be H or $CH_3$,
Structure 7 wherein each of $R_1$-$R_6$ is independently H or $CH_3$, or
Structure 8 wherein each of $R_1$-$R_7$ is independently H or $CH_3$. In some embodiments, the polyamine is of Structure 4 and is 1,4,7-Trimethyl-1,4,7-triazacyclononane. In some embodiments, the is of Structure 1 and is 1, 2-Ethanediamine, N1-(2-aminoethyl) or 1, 2-Ethanediamine, N1-[2-(dimethylamino) ethyl]-N1, N2, N2-trimethyl-. In some embodiments, the polyamine is 1, 2-Ethanediamine, N1-[2-(dimethylamino) ethyl]-N1, N2, N2-trimethyl-. In some embodiments, the polyamine is of Structure 2, and is N,N,N',N'-Tetramethyl-1,3-propanediamine. In some embodiments, the glycans have been labeled by being reacted with 8-aminopyrene-1, 3,6-trisulfonic acid ("APTS"), InstantQ™, or 8-Aminonaphthalene-1,3,6-trisulfonic acid disodium salt ("ANTS"). In some embodiments, the glycans have been labeled with APTS and are MAN-5 glycan and A1F. In some embodiments, the glycans further include G0. In some embodiments, the glycans have been labeled with InstantQ™ and are MAN-5 glycan and A1F. In some embodiments, the glycans further include G0F-N.

In another groups of embodiments, the invention provides compositions for capillary electrophoretic separation of labeled glycans, which comprise a gel suitable for capillary gel electrophoresis of labeled glycans, which gel comprises at least one polyamine of any of the following structures
Structure 1 wherein each of $R_1$-$R_3$ are independently selected from H and $CH_3$,
Structure 2 wherein $R_1$ and $R_2$ are independently selected from H and $CH_3$,
Structure 3 wherein each $R_1$ and $R_2$ are independently selected from H and $CH_3$,
Structure 4 wherein each of $R_1$-$R_3$ is independently selected from H and $CH_3$,
Structure 5 wherein each of $R_1$-$R_4$ is independently selected from H and $CH_3$, Structure 6, wherein each of $R_1$-$R_6$ is independently selected from H and $CH_3$, Structure 7 wherein each of $R_1$-$R_6$ is independently H or $CH_3$, or

Structure 8 wherein each of $R_1$-$R_7$ is independently H or $CH_3$.

In some embodiments, the polyamine is of Structure 4 and is 1,4,7-Trimethyl-1,4,7-triazacyclononane. In some embodiments, the polyamine is of Structure 1 and is 1, 2-Ethanediamine, N1-(2-aminoethyl) or 1, 2-Ethanediamine, N1-[2-(dimethylamino) ethyl]-N1, N2, N2-trimethyl-. In some embodiments, the polyamine is N,N,N',N",N"-Pentamethyldiethylenetriamine. In some embodiments, the polyamine is of Structure 2, and is N,N,N',N'-Tetramethyl-1,3-propanediamine. In some embodiments, the gel suitable for capillary gel electrophoresis of labeled glycans comprises polyethylene oxide.

In another group of embodiments, the invention provides cartridges or capillaries loaded with a gel for capillary electrophoretic separation of labeled glycans, which gel comprises at least one polyamine of any of the following structures:

Structure 1 wherein each of $R_1$-$R_3$ are independently selected from H and $CH_3$, Structure 2 wherein $R_1$ and $R_2$ are independently selected from H and $CH_3$,

Structure 3 wherein each $R_1$ and $R_2$ are independently selected from H and $CH_3$, Structure 4 wherein each of $R_1$-$R_3$ is independently selected from H and $CH_3$, Structure 5 wherein each of $R_1$-$R_4$ is independently selected from H and $CH_3$, or Structure 6, wherein each of $R_1$-$R_6$ is independently selected from H and $CH_3$, Structure 7 wherein each of $R_1$-$R_6$ is independently H or $CH_3$, or

Structure 8 wherein each of $R_1$-$R_7$ is independently H or $CH_3$. In some embodiments, the polyamine is of Structure 4 and is 1,4,7-Trimethyl-1,4,7-triazacyclononane. In some embodiments, the polyamine is of Structure 1 and is 1, 2-Ethanediamine, N1-(2-aminoethyl) or 1, 2-Ethanediamine, N1-[2-(dimethylamino) ethyl]-N1, N2, N2-trimethyl-. In some embodiments, the polyamine is N,N,N',N'',N''-Pentamethyldiethylenetriamine. In some embodiments, the polyamine is of Structure 2, and is N,N,N',N'-Tetramethyl-1,3-propanediamine. In some embodiments, the gel further comprises polyethylene oxide. In some embodiments, the cartridge or capillary is a cartridge. In some embodiments, the cartridge or capillary is a capillary.

In yet a further group of embodiments, the invention provides kits for capillary electrophoretic separation of labeled glycans, comprising a cartridge, a capillary, or both a cartridge and a capillary, loaded with a gel suitable for capillary gel electrophoresis of labeled glycans, which gel further comprises an effective amount of at least one polyamine of any of the following structures: Structure 1 wherein each of $R_1$-$R_3$ are independently selected from H and $CH_3$, Structure 2 wherein $R_1$ and $R_2$ are independently selected from H and $CH_3$,

Structure 3 wherein each $R_1$ and $R_2$ are independently selected from H and $CH_3$, Structure 4 wherein each of $R_1$-$R_3$ is independently selected from H and $CH_3$, Structure 5 wherein each of $R_1$-$R_4$ is independently selected from H and $CH_3$, Structure 6, wherein each of $R_1$-$R_6$ is independently selected from H and $CH_3$, Structure 7 wherein each of $R_1$-$R_6$ is independently H or $CH_3$, or Structure 8 wherein each of $R_1$-$R_7$ is independently H or $CH_3$, and (b) a label for labeling glycans to be separated by capillary electrophoresis. In some embodiments, the polyamine is of Structure 4 and is 1,4,7-Trimethyl-1,4,7-triazacyclononane. In some embodiments, the polyamine is of Structure 1 and is 1, 2-Ethanediamine, N1-(2-aminoethyl) or 1, 2-Ethanediamine, N1-[2-(dimethylamino)ethyl]-N1, N2, N2-trimethyl-. In some embodiments, the polyamine is N,N,N',N'',N''-Pentamethyldiethylenetriamine. In some embodiments, the polyamine is of Structure 2, and is N,N,N',N'-Tetramethyl-1,3-propanediamine. In some embodiments, the gel further comprises an effective amount of polyethylene oxide. In some embodiments, the label is APTS or InstantQ™. In some embodiments, the kit further comprises glycan standards or labeled glycan standards. In some embodiments, the cartridge, capillary, or both a cartridge and a capillary, is a cartridge. In some embodiments, the cartridge, capillary, or both a cartridge and a capillary, is a capillary.

BRIEF DESCRIPTION OF THE DRAWINGS

FIG. 1.

FIG. 2.

DETAILED DESCRIPTION

As set forth in the Background, determining which carbohydrates, or glycans, are attached to a glycoconjugate, such as a glycoprotein is important to understanding the pharmacokinetics, immunogenicity, and potential therapeutic effectiveness of the glycoprotein. Accordingly, determining which glycans are attached to a given glycoprotein has become an important regulatory question for glycoproteins, such as antibodies and other biologics intended for therapeutic use.

One family of techniques for analyzing various types of compounds is capillary electrophoresis, or "CE." There are a number of varieties of CE, including capillary gel electrophoresis, or "CGE," which separates molecules based on molecular size, and capillary zone electrophoresis, or "CZE," which separates molecules based on charge:mass ratio. CE in general, and CGE in particular, are well known in the art and are taught in a number of references, including Beckman Coulter's booklet "Introduction to Capillary Electrophoresis" (undated, but from 1991-2), Whatley, H., Basic Principles and Modes of Capillary Electrophoresis, in Petersen and Mohammad, eds., Clinical and Forensic Applications of Capillary Electrophoresis, Humana Press, Inc. Totowa, NJ (2001), and Lauer and Rozing, eds., High Performance Capillary Electrophoresis, $2^{nd}$ Ed., Agilent Technologies, Inc., Santa Clara, CA (2014). CGE has been used for decades to separate proteins and nucleic acids. See, e.g., Zhu et al., Anal Chim Acta. 2012 Jan. 4; 709: 21-31. The high structural diversity of glycans, and particularly of N-glycans, however, has made the separation and characterization of glycans more challenging than is the separation and detection of proteins and nucleic acids. Schwarzer, et al., "N-glycan analysis by CGE-LIF: Profiling influenza A virus hemagglutinin N-glycosylation during vaccine production," Electrophoresis 2008, 29, 4203-4214, at 4204. Typically, glycans to be analyzed by CGE are labeled with a charged fluorophore or UV-visible dye to allow electromigration and detection by laser induced fluorescence ("LIF") or by UV light, respectively. See, e.g., Schwarzer, supra, Reusch, et al., High-throughput glycosylation analysis of therapeutic immunoglobulin G by capillary gel electrophoresis using a DNA analyzer," 2014, doi: 10.4161/mabs.26712.

While standard CE techniques have given good separation of many glycans, analysis of some labeled glycans has been hindered by the fact that some glycans co-migrate with each other. Reducing co-migration of labeled glycans would improve resolution of the glycans present in the sample being analyzed. Unfortunately, to date, compositions and methods for reducing co-migration of labeled glycans, and thus for improving resolution, have not been reported.

For example, mammalian antibodies and fusion proteins are important, and very expensive, groups of therapeutics, and are typically produced in commercial fermentation systems. Monitoring of the levels of MAN-5 glycan (Mannopentaose-di-(N-acetyl-D-glucosamine), or "Oligomannose-5 glycan", CAS No. 66091-47-2, sometimes also referred to as "Man5"), during production of the antibody or fusion protein can serve as a marker that the fermentation system is under stress and allow intervention, hopefully in time to save the production lot. The following structure for MAN-5 glycan is taken from the Sigma-Aldrich website (Sigma-Aldrich, St. Louis, MO):

Surprisingly, we have now found that the presence of selected polyamines in the gel matrix during CGE analysis of labeled glycans improves the resolution of important labeled glycans, such as MAN-5 glycan, from other glycans which otherwise can co-migrate with the labeled glycan of interest. In studies underlying the present disclosure, MAN-5 glycan was labeled with either a label commonly used in CGE, 8-aminopyrene-1,3,6-trisulfonic acid ("APTS"), CAS No. 196504-57-1, or with InstantQ™ (ProZyme, Inc., Hayward, CA), a commercially available label which does not require the use of reductive amination, which requires no drying steps after solid phase extraction cleanup, and which reduces the need for using toxic reagents. Glycans labeled with either label may be subjected to CGE using a capillary with an inner coating and a gel matrix containing an exemplar polyamine.

Two polyamines of Structure 1 below were tested. Surprisingly, each of the polyamines resulted in electropherograms (the plot of results of separations resulting from a capillary gel electrophoresis) that improved the ability to resolve the labeled MAN-5 glycan from other labeled glycans present in the sample. Importantly, the increase in resolution of the labeled MAN-5 glycan did not come at the cost of reducing the ability to see the separation of other labeled glycans in the sample. This was itself surprising, as in initial studies, a large polyamine was used and found not to result in substantially improved resolution of labeled MAN-5 glycan, but changed parts of the electropherogram for other glycans in the sample in ways that interfered with their interpretation. In particular, the peaks for sialylated glycans collapsed and resulted in earlier relative migration times which were close to the dye peak (in general, practitioners want peaks representing to be at a distance from the peak for any unconjugated or hydrolyzed dye left in the system that does not represent dye attached to a glycan of interest), and peaks for larger, neutral glycans were broadened. The larger polyamines of the structures set forth below surprisingly provided not only excellent separation of MAN-5 glycan, but also a satisfactory electropherogram of other labeled glycans in the sample. In the studies underlying the present disclosure, the polyamine was present in the gel, not in the buffer. As persons of skill will appreciate, CGE is conducted using a capillary filled with the gel of choice. Unlike CZE, the gel is not replenished by buffer during the electrophoresis. Accordingly, in preferred embodiments, the polyamine is used in the gel, but not in any buffer that may be used during the electrophoretic separation.

Given the results in improving resolution of MAN-5 glycan by CGE, we expect similar results in improving resolution of other labeled glycans of interest using other polyamines of the structures noted below. As persons of skill will appreciate, the other labeled glycans that will co-migrate with a particular labeled glycan of interest in a CGE separation will be dependent in part on the particular label used, as the different labels used in the art typically are different in size and charge. Whether the resolution of any particular labeled glycan of interest will be improved by the presence of any particular polyamine of the structures taught below, or by a particular concentration of one of those polyamines in the CGE gel, can be readily determined. For example, a sample containing a known amount of MAN-5 glycan labeled by a label of choice can be subjected to CGE using a gel with the particular polyamine of choice, at a desired concentration. One or more other known amounts of labeled glycans that are suspected of being able to co-migrate with MAN-5 glycan when subjected to CGE are then subjected to CGE using the same gel composition, the same polyamine, and the same concentration of that polyamine. The same amount of MAN-5 glycan, labeled the same way, and the same amounts of the other glycans, labeled the same way, are then combined and run together in a CGE analysis using the same gel composition and same concentration of the same polyamine as used in the preceding analyses mentioned. If the amount of labeled MAN-5 glycan detected in the first CGE can still be determined from the electropherogram resulting from the CGE of the labeled glycans when combined, then that particular polyamine is successful at preventing co-migration of labeled glycans that might interfere with resolution of the labeled MAN-5 glycan in the sample. The same assay can also be readily used by the practitioner to test a selected coating for the capillary or a gel to use as the sieving matrix.

Given the results using CGE, it is expected that similar results will be obtained using other forms of CE that use a gel for size separation of analytes, including hybrid techniques. In preferred embodiments, the CE technique is CGE.

The polyamines are conveniently introduced into the gel composition as a solution, but can be mixed as a powder into the buffer used to form the gel matrix, or introduced by other convenient means known in the art. In studies underlying the present disclosure, the polyamine was added in a 5% aqueous solution (v/v). To titrate amounts of polyamine that would be useful, polyamine was added in amounts ranging from 5 µl to 100 µl (depending on the polyamine being tested) to 5 ml to 7 ml of ingredients for the gel recipe (the amount of gel in our initial tests was 5 ml, and later tests was increased to 7 ml), so that the polyamine was uniformly distributed in the gel. An improvement of resolution of the test glycan (in these studies, MAN-5 glycan] was seen at lower concentrations for larger polyamines or for polyamines with more polyamines compared to smaller polyamines or polyamines with fewer amine groups (for example, polyamines with three amine groups needed a higher concentration to show an increase in resolution of the labeled glycans that a polyamine with four amine groups). Above a certain concentration for the polyamine, about 90 µl per 7 ml for certain polyamines tested, the current went above the amount recommended for the apparatus, and therefore above the amount usable for the CGE separation. In studies underlying the present disclosure, 70 µl of a 5% solution of the test polyamine, N,N,N',N'-Tetramethyl-1,3-propanediamine ("PDA"), CAS No. 110-95-2, was found to be effective in 7 ml of gel.

A typical polyamine containing 3 amine groups is typically added to the gel recipe in a 5% solution. Such a solution is typically added to the gel recipe in amounts of about 0.5 µl to 20 µl, with "about" meaning±0.1 µl. A typical polyamine containing 4 amine groups is typically added to the gel recipe in a 1% solution, in the same amounts as noted above. We expect that a polyamine containing 5 amine groups will be added a more dilute solution, at the same volumes as noted above. Any particular amount of any particular polyamine can be readily tested for its effect in improving resolution of labeled glycans of interest, such as Man5, A1F and G0, by subjecting the labeled glycans to CGE with the test amount of the test polyamine to see if the gel succeeds in separating the different labeled glycans of interest from one another. Any particular polyamine can be tested by performing a series of such titering to determine amounts that give good separation of the labeled glycans of interest. Glycans labeled by labels other than APTS or InstantQ™ can likewise be used to determine whether a particular amount of a particular polyamine succeeds in separating the different glycans from one another. Finally, more than one polyamine can be used to improve resolution of the labeled glycans. Determining amounts of the respective polyamines of interest to use can readily be determined by simply mixing the polyamines into the gel recipe in different amounts to see which combination or range of combinations succeed in separating the different labeled glycans of interest from one another.

As persons of skill are aware, there are several types of CE. While all types share certain basic features (the use of a capillary and an electrophoretic separation), they also have significant differences and cannot be treated as simple substitutes for one another. CGE, also known as "capillary sieving electrophoresis," uses a sieving matrix to separate analytes by size, and therefore differs from CE techniques such as capillary zone electrophoresis, or "CZE," which instead use a background electrolyte solution and separate analytes by charge:mass ratio. There are also "hybrid" CE techniques which also use a sieving matrix. Due to the various differences between CE using sieving matrices and CE techniques which do not, it cannot be predicted that reagents that improve resolution in a technique that does not employ a sieving matrix, such as CZE, will have the same or even a similar effect if used in a CE technique that uses a sieving matrix, such as CGE, or vice versa.

In studies underlying the present disclosure, it was shown not only that the presence of polyamines in the sieving matrix, or gel, during a CGE procedure improved the resolution of labeled glycans in the sample, but also that the presence of some polyamines were surprisingly better than were others. As noted above, the presence of a quaternary polyamine in the CGE gel with a large separation between the nitrogens resulted in some improvement in resolution of labeled MAN-5 glycan, but resulted in peak profiles that were undesirably collapsed for the sialylated glycans and broadened for the large neutral glycans. When a tertiary polyamine was tested, however, there was surprisingly, both a better improvement in resolution of the labeled MAN-5 glycan, without degradation of the electropherogram of other labeled glycans present in the sample.

The polyamine ethylenediamine (1,2-diaminoethane) should not be used as the polyamine, as we found the conductivity to be too high for use in CGE systems.

In view of the results obtained in studies underlying the present disclosure, we expect polyamines of the types described herein to improve resolution of labeled N-glycans, labeled O-glycans, of labeled sialic acids, of milk oligosaccharides, and of labeled monosaccharides.

In some embodiments, the polyamine is a compound of Structure 1:

Structure 1 wherein each of $R_1$-$R_3$ are independently H or $CH_3$. In a particularly preferred embodiment, the compound of Structure 1 is 1, 2-Ethanediamine, N1-(2-aminoethyl), CAS No. 111-40-0. In another particularly preferred embodiment, the compound of Structure 1 is 1, 2-Ethanediamine, N1-[2-(dimethylamino) ethyl]-N1, N2, N2-trimethyl-, CAS No. 3030-47-5. In another particularly preferred embodiment, the compound of Structure 1 is 2,6,10-trimethyl-2,6,10-trizaundecane, CAS NO. 3855-32-1. This compound is so potent that it can be used at lower concentrations.

In some embodiments, the polyamine is a compound of Structure 2:

Structure 2 wherein $R_1$ and $R_2$ are independently selected from H and $CH_3$. In a particularly preferred embodiment, the compound of Structure 2 is N,N,N',N'-Tetramethyl-1,3-propanediamine ("PDA"), CAS No. 110-95-2. PDA seems to give particularly good results when used with the dye APTS. The compound of structure 2 cannot be ethylenediamine (1,2-diaminoethane) or cadaverine (1,5-diaminopentane), although methylated cadaverine can be used.

In some preferred embodiments, the polyamine is a compound of Structure 3:
Structure 3 wherein $R_1$ and $R_2$ are independently selected from H and $CH_3$.

In some preferred embodiments, the polyamine is a compound of Structure 4: Structure 4 wherein each of $R_1$-$R_3$ is independently H or $CH_3$. Compounds of these structures may be referred to as "tacns". In some preferred embodiments, the polyamine of Structure 4 is 1,4,7-Trimethyl-1,4,7-triazacyclononane (CAS No. 96556-05-7).

In some preferred embodiments, the polyamine is a compound of Structure 5:
Structure 5 wherein each of $R_1$-$R_4$ is independently H or $CH_3$.

In some embodiments, the polyamine is a tetranitrogen adamantane compound of Structure 6:
Structure 6 wherein each of $R_1$-$R_6$ is independently H or $CH_3$. In a preferred embodiment, the compound of structure 6 is hexamethylenetetramine, CAS No. 100-97-0.

In some embodiments, the polyamine is a linear tetraamine compound of Structure 7:
Structure 7 wherein each of $R_1$-$R_6$ is independently H or $CH_3$.

In some embodiments, the polyamine is a linear pentaamine of Structure 8:
Structure 8 wherein each of $R_1$-$R_7$ is independently H or $CH_3$. Structures 7 and 8 are expected to be useful in particular in the separation of sialylated glycans.

In the course of the present work, several CE procedures were noted in which polyamines were used in CZE buffers for the separation of proteins. For example, U.S. Pat. No. 9,222,913 teaches the use of certain polyamines, particularly small ones, to reduce electro-osmotic flux in separating hemoglobin molecules (protein chains with one or more sugars attached). As persons of skill will appreciate, the labeled glycans which are the molecules separated in CGE procedures in the inventive methods are carbohydrates, which have very different structural, functional and physical properties than those of the glycated proteins investigated in the '913 patent. Further, while both the '913 patent and the present disclosure involve the use of electrophoretic techniques, the technique used in the '913 patent and the technique used in the present disclosure are different techniques using different systems that are directed to different physical properties of the molecules being separated and analyzed by the system. Similarly, Lucy et al., "Non-covalent capillary coatings for protein separations in capillary electrophoresis," Journal of Chromatography A, 1184 (2008) 81-105, teaches that amines can reduce the adsorption of proteins to fused silica capillary walls. This is of limited relevance to the separation of glycans, which are not expected to bind to capillary walls.

Definitions

As used herein, the phrases "gel," "gel matrix," and "sieving matrix" are synonyms.

In the context of performing CGE or hybrid CE procedures using a gel, the term "resolution" refers to the ability to distinguish between two analytes that would otherwise migrate together in the analytical system being used to separate them. For convenience of reference, the term "CGE" as used herein includes hybrid CE procedures using a gel unless otherwise required by context The term "label," with regard to labeling a glycan, means chemically attaching to the glycan a fluorescent moiety or a UV-visible dye.

The phrase "glycans have been labeled by being reacted with" a named compound means that the label attached to a labeled glycan is the label that remains after a glycan has been contacted with the named compound under conditions allowing it to label the glycan with a fluorescent moiety or a UV-visible dye.

CE and CGE

Capillary electrophoresis and CGE have been used to separate various analytes for over two decades. It is therefore expected that practitioners are familiar with the various protocols and reagents used in performing CGE and hybrid CE methods using gels. CE in general, and CGE in particular, are discussed in detail in texts such as "Capillary Electrophoresis Methods for Pharmaceutical Analysis," Volume 9, Ahuja and Jimidar, eds., Elsevier, London (2008), "Capillary Electrophoresis Guidebook: Principles, Operation, and Applications," (Methods in Molecular Biology), Altria, ed., Humana Press, Totowa, NJ (2010), and "Capillary Electrophoresis: Methods and Potentials," Engelhardt et al., eds., Friedr, Vieweg & Sohn, Braunschweig/Wiesbaden (1996). CE of carbohydrates in particular is also taught in a number of texts, including "Capillary Electrophoresis of Carbohydrates" (Methods in Molecular Biology, Vol. 213), Thibault and Honda, eds., Humana Press Inc., Totowa, NJ (2003), "Capillary Electrophoresis of Carbohydrates: From Monosaccharides to Complex Polysaccharides," Volpi, ed., Humana Press, Totowa, NJ (2011) and "Carbohydrate Analysis: High Performance Liquid Chromatography and Capillary Electrophoresis," El Rassi, ed., Elsevier Science B.V., Amsterdam, the Netherland (1995). Chapter 8 of this last reference discusses the use of a variety of CE techniques, including both CZE and CGE, for the analysis of carbohydrates and glycoconjugates.

Cartridges, Gels and Dyes

Gels for CGE of glycans are known in the art. Typically, gels for separating glycans differ from those for separating proteins. For example, gels for separating proteins typically contain sodium dodecyl sulfate and much higher levels of detergents than are used in gels for glycan separation, to keep the proteins completely denatured. The methods for preparing gels for protein separations also differ from those for glycan separations, as gels for protein separation are typically subjected to a regeneration procedure.

In preferred embodiments, the gels used in the inventive CGE methods and compositions can be as taught in U.S. Pat. No. 8,163,152 (the "'152 Patent"), at col. 12, lines 15-23. In some preferred embodiments, the gel is made following the recipe set forth in the '152 patent at col. 12, lines 25-35, with the following modifications: (1) the polyethylene oxide ("PEO") of 7000000 mwt g/mol set forth in the recipe was replaced by PEO of 8000000 mwt g/mol, as PEO of 7000000 molecular weight is currently not commercially available, and (2) the EtBr is omitted (this modified recipe is sometimes referred to herein as the "modified PEO gel"). In some embodiments, the mwt g/mol of the larger and the smaller PEOs set forth in the recipe can independently be ±20% of the mwt g/mol values stated. And, regardless of the size of the PEOs used, EtBr is preferably omitted from the gel. While the entirety of the '152 Patent is incorporated by reference, the portions cited above are specifically incorporated by reference. As persons of skill are aware, "PEO" and "polyethylene glycol," or "PEG," are chemically synonymous, but "PEG" is typically used to refer to polymers below 20,000 g/mol, while "PEO" is typically used to refer to polymers above that point. The studies underlying the present invention were conducted using the modified PEO gel recipe noted above.

In some embodiments, the gel may be composed of a compound other than PEO used for capillary gel electrophoresis of glycans, such as hydroxypropylmethylcellulose (HPMC). While PEO is a particularly preferred gel, other neutral hydrophilic polymers, such as alkyl celluloses, polyvinyl alcohol, dextrans, or polyacrylamide, may be used.

Gel used for CGE analysis of glycans may be created by any means known in the art. Conveniently, the gels are provided in a cartridge. The cartridges are typically used in an analytical instrument configured to accept them, such as the gel cartridges configured for use in a GL1000 glycan analyzer (BiOptic Inc., New Taipei City, Taiwan (R.O.C)), and allow quick changes of gels, expediting a series of analyses. The polyamines are conveniently added to the reagents before the gel is formed to allow even distribution of the polyamine within the gel. Typically, the gel is made in bulk, dispensed into cartridges, and cartridges already filled with the gel of choice are then purchased by the practitioner intending to use the cartridge to perform CGE separations in an instrument configured to receive the cartridge. The cartridges act as reservoirs from which the gel in one or more capillaries is replenished between electrophoretic separations run in the instrument.

The Examples discuss the use of the glycan labels APTS and InstantQ™ (ProZyme, Inc., Hayward, CA). ANTS (typically purchased as 8-Aminonaphthalene-1,3,6-trisulfonic acid disodium salt, the sodium salt hydrate, CAS No. 5398-34-5), and other polysulfonate labels for glycans can also be used.

Capillaries and Coatings

Capillaries used for CGE are typically made of fused silica, with inner diameters of 200 microns or less. To reduce variables, the studies underlying the present invention all used capillaries with an internal diameter of 75 microns.

Studies underlying the present disclosure indicated that uncoated fused silica capillaries were not suitable for separating glycans using a PEO gel. Accordingly, coated capillaries are preferred. Coatings suitable for use in separating glycans are known in the art, as exemplified by T. Kubo, et al., "Tunable separations based on a molecular size effect for biomolecules by poly(ethyleneglycol) gel-based capillary electrophoresis," J. Chromatogr. A (2017), http://dx.doi.org/10.1016/j.chroma.2017.06.043.

Separation of MAN-5 Glycan from Other Glycans

Figure 2:
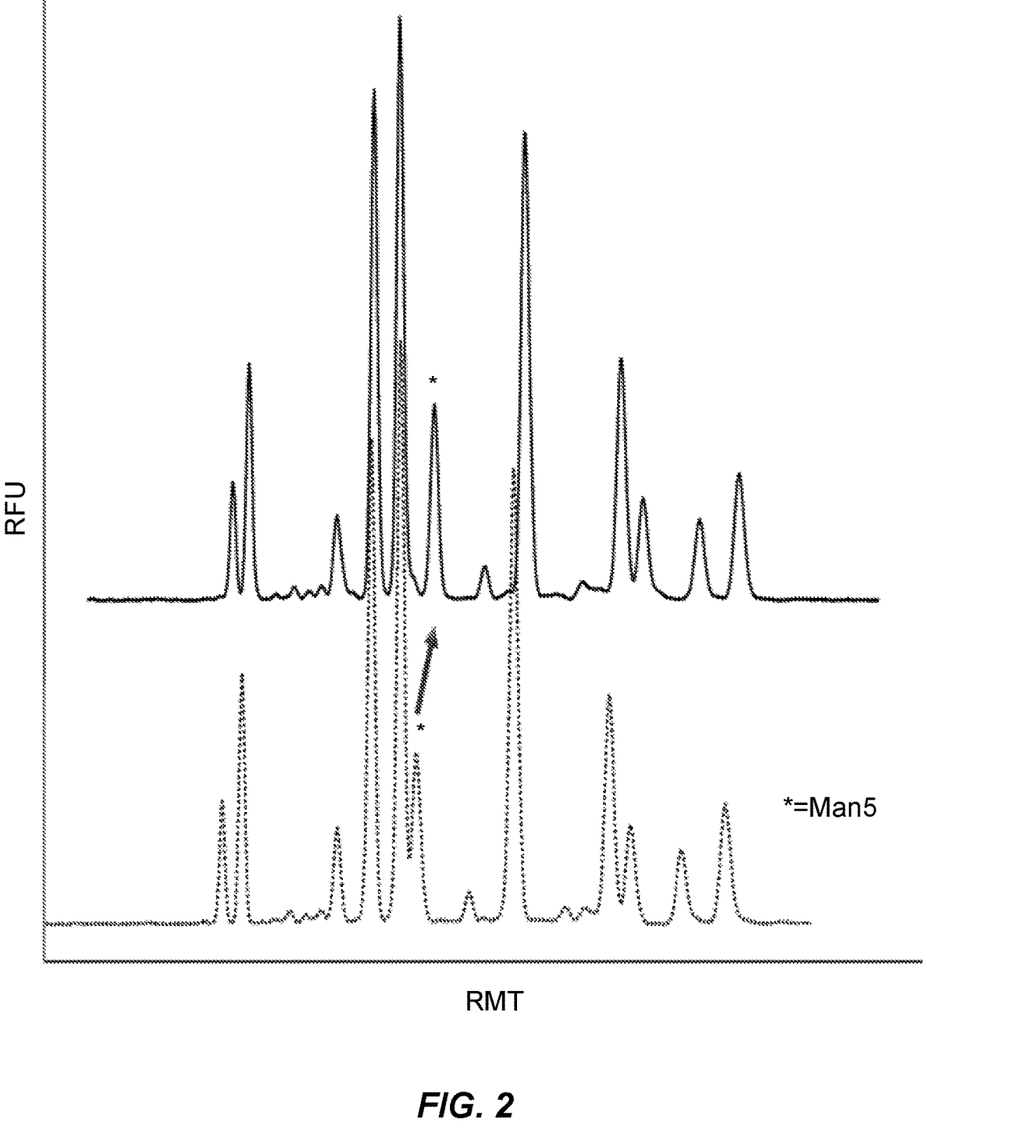
FIG. 2 presents electropherograms showing the capillary gel electrophoresis separation of glycans released from etanercept, a fusion protein of the TNF receptor fused to the constant end of the IgG1 antibody. The glycans were released by enzymatic digestion with PNGase F and labeled with the label InstantQ™. They were then subjected to CGE in a gel either (a) containing an exemplar polyamine (solid line, top), or (b) not containing the polyamine (dashed line, bottom). "RFU": "relative fluorescence units." "RMT": "relative migration time." Asterisk denotes peak for Man5 glycan, which is also designated by an arrow pointing to the peak for Man5 in the top line.

As noted in a preceding section, changes in the level of MAN-5 glycan in a fermenter can signal stress in the fermentation reaction which could result in loss of an entire production run of a valuable therapeutic agent, such as one of the antibodies approved by the FDA as an anti-cancer therapeutic. Accordingly, it has become important to determine the amount of MAN-5 glycan present in the system. Unfortunately, monitoring the amount of MAN-5 glycan by CGE has been difficult because other glycans can be present that co-migrate with MAN-5 glycan using conventional CGE gels. The particular glycans that co-migrate with MAN-5 glycan when the g7lycans are labeled with APTS are G0 and A1F. The glycans that co-migrate with MAN-5 glycan when the glycans are labeled with InstantQ™ are G0F-N and A1F. As shown in FIG. 2 (discussed in Example 2, below), the presence of an exemplar polyamine in an exemplar CGE gel sharply improved the resolution of MAN-5 glycan from A1F compared to a CGE using the same glycans and the same gel, but without the polyamine in the gel.

EXAMPLES

Example 1

Capillary gel electrophoresis separations were performed using G0F-N and Man5 glycans labeled with a commercially available label, InstantQ™ (ProZyme, Inc., Hayward, CA), in the presence of two different polyamines. CGE with InstantQ™ has better separation of glycans than APTS, so G0F-N is separated into two isoforms, depending on the arm to which the GlcNAc is attached (that is, the [3] or [6] arm of the biantennary). APTS does not separate these isoforms structures in the system used for this study.

Figure 1:
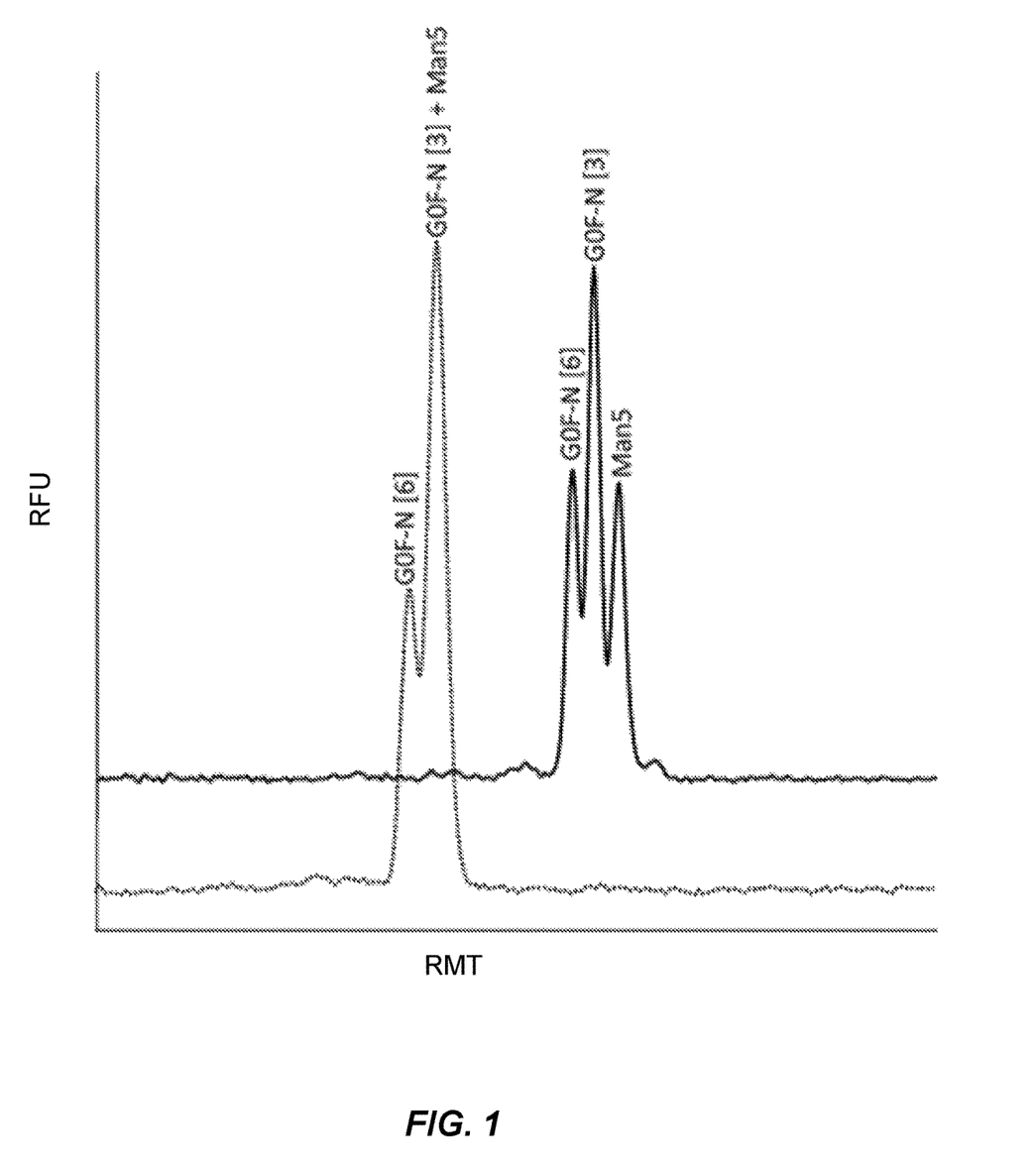
FIG. 1 presents electropherograms of the capillary gel electrophoresis separation of G0F-N and Man5 glycans labeled with the label InstantQ™ (ProZyme, Inc., Hayward, CA). The lower, dotted line, shows the electropherogram of a mixture of labeled glycan standards G0F-N[3] and Man5 analyzed on a gel spiked with N,N,N',N'-Tetramethylethylenediamine (CAS No. 110-18-9) at 1.0 µl/ml gel. As shown on the electropherogram, this polyamine did not help separate the G0F-N[3] and Man5, which co-migrated. In a separate preparation, the gel was spiked with N,N,N',N'-Tetramethyl-1,3-propanediamine (CAS No. 110-95-2) at a concentration of 0.50 µl per ml of gel. The electropherogram of the separation using this gel is shown in the upper, solid line. The presence of this polyamine shifted Man5 away from G0F-N[3] and significantly improved the resolution of the Man5 from the G0F-N[3]. RFU": "relative fluorescence units." "RMT": "relative migration time."

The results are shown in FIG. 1. The lower, dotted line in FIG. 1 shows the electropherogram of a mixture of labeled glycan standards G0F-N and Man5 analyzed on a gel spiked with EDA (N,N,N',N'-Tetramethylethylenediamine, CAS No. 110-18-9) at 1.0 μl/ml gel. As shown by the lower, dotted line on the electropherogram, the presence of EDA did not help separate the G0F-N[3] and Man5, which co-migrated.

In a separate preparation, the gel was spiked with PDA (N,N,N',N'-Tetramethyl-1,3-propanediamine, CAS No. 110-95-2) at a concentration of 0.50 μl per ml of gel. The electropherogram of the separation using this gel is shown in the upper, solid line of FIG. 1. As shown by the upper, solid line on FIG. 1, the presence of the PDA polyamine shifted Man5 away from G0F-N[3] and significantly improved the ability to differentiate Man5 from G0F-N[3] present in the sample.

Example 2

Etanercept, a fusion protein of the TNF receptor fused to the constant end of the IgG1 antibody, was enzymatically deglycosylated by PNGase F. Glycans released from the protein were labeled by InstantQ™ (ProZyme, Inc., Hayward, CA), and were analyzed by CGE using two gels, one with an exemplar polyamine, and a second gel made following the same recipe, but without the polyamine. The gel with the polyamine was spiked with the exemplar polyamine 1,4,7-Trimethyl-1,4,7-triazacyclononane (Sigma-Aldrich, St. Louis, MO, product 311294, Pubchem substance ID 24858510), at a concentration of 0.86 μl per ml gel.

The results are shown in FIG. 2. Referring to FIG. 2, the peak for MAN-5 glycan is designated by an asterisk and, for the top line, an arrow. The peak to the immediate left of the MAN-5 glycan peak is the peak for the glycan A1F. The upper, solid line in FIG. 2 sets forth the electropherogram of glycan separation using the gel containing the polyamine, while the lower, dotted line shows the results using the gel made following the same recipe, but without the polyamine. The line shows a shift of Man5 away from the shoulder compared to the gel without the polyamine being present. Further, the peak for Man5 in the upper line (from the gel containing the polyamine) returns to the baseline, facilitating the ability to quantitate the amount of Man5 present. Accordingly, the presence of the polyamine in the assay notably improved the resolution of MAN-5 glycan compared to the same assay without the polyamine being present.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A method of improving resolution in separating labeled glycans in a sample by capillary electrophoresis analysis, wherein said separation takes place in a gel, wherein said gel comprises a polyamine having a structure of any of Structure 1

Structure 1 wherein $R_1$, $R_2$, and $R_3$ are independently selected from H and $CH_3$,

Structure 2

Structure 2 wherein each of $R_1$ and $R_2$ is independently selected from H and $CH_3$, and said polyamine is N,N,N',N'-Tetramethyl-1,3-propanediamine,

Structure 3

Structure 3 wherein each of $R_1$ and $R_2$ is independently selected from H and $CH_3$,

Structure 4

Structure 4 wherein each of $R_1$-$R_3$ is independently selected from H and $CH_3$, Structure 5

Structure 5 wherein each of $R_1$-$R_4$ can independently be H or $CH_3$,
Structure 6,

Structure 6 wherein each of $R_1$-$R_6$ can independently be H or $CH_3$,
Structure 7

Structure 7 wherein each of $R_1$-$R_6$ is independently H or $CH_3$, or
Structure 8

Structure 8 wherein each of $R_1$-$R_7$ is independently H or $CH_3$, provided that, when said separation takes place in a capillary containing the gel and the gel is of polyethylene oxide ("PEO"), the capillary is coated.

2. The method of method 1, wherein said polyamine is of Structure 4 and is 1,4,7-Trimethyl-1,4,7-triazacyclononane.

3. The method of claim 1, wherein said polyamine is of Structure 1 and is 1, 2-Ethanediamine, N1-(2-aminoethyl) or 1, 2-Ethanediamine, N1-[2-(dimethylamino) ethyl]-N1, N2, N2-trimethyl-.

4. The method of claim 3, wherein said polyamine is 1, 2-Ethanediamine, N1-[2-(dimethylamino) ethyl]-N1, N2, N2-trimethyl-.

5. The method of claim 1, wherein said glycans have been labeled by being reacted with 8-aminopyrene-1,3,6-trisulfonic acid ("APTS"), or 8-Aminonaphthalene-1,3,6-trisulfonic acid disodium salt ("ANTS").

6. The method of claim 5, wherein the glycans have been labeled with APTS and are MAN-5 glycan and A1F glycan.

7. The method of claim 5, wherein the glycans have been labeled with ANTS and are MAN-5 glycan and A1F glycan.

8. A composition for capillary electrophoretic separation of labeled glycans, said composition comprising a gel suitable for capillary gel electrophoresis of labeled glycans, which gel comprises at least one polyamine of any of the following structures:

Structure 1

Structure 1 wherein each of $R_1$-$R_3$ are independently selected from H and $CH_3$,

Structure 2

Structure 2 wherein $R_1$ and $R_2$ are independently selected from H and $CH_3$, and said polyamine is N,N,N',N'-Tetramethyl-1, 3-propanediamine,

Structure 3

Structure 3 wherein each $R_1$ and $R_2$ are independently selected from H and $CH_3$,

Structure 4

Structure 4 wherein each of $R_1$-$R_3$ is independently selected from H and $CH_3$, Structure 5 wherein each of $R_1$-$R_4$ can independently be H or $CH_3$,

Structure 6, wherein each of $R_1$-$R_6$ can independently be H or $CH_3$,

Structure 7 wherein each of $R_1$-$R_6$ is independently H or $CH_3$, or

Structure 8 wherein each of $R_1$-$R_7$ is independently H or $CH_3$, provided that, when the capillary electrophoresis separation takes place in a capillary containing the gel and the gel is of polyethylene oxide ("PEO"), the capillary is coated.

9. The composition of claim 8, wherein said polyamine is of Structure 4 and is 1,4,7-Trimethyl-1,4,7-triazacyclononane.

10. The composition of claim 8, wherein said polyamine is of Structure 1 and is 1, 2-Ethanediamine, N1-(2-aminoethyl) or 1, 2-Ethanediamine, N1-[2-(dimethylamino) ethyl]-N1, N2, N2-trimethyl-.

11. The composition of claim 8, wherein said polyamine is N,N,N',N'',N''-Pentamethyldiethylenetriamine or N,N,N',N'-Tetramethyl-1,3-propanediamine.

12. The composition of claim 8, wherein said gel suitable for capillary gel electrophoresis of labeled glycans comprises polyethylene oxide.

13. A cartridge or capillary loaded with a gel for capillary electrophoretic separation of labeled glycans, which gel comprises at least one polyamine of any of the following structures:

Structure 1 wherein each of $R_1$-$R_3$ are independently selected from H and $CH_3$, Structure 2 wherein $R_1$ and $R_2$ are independently selected from H and $CH_3$, and said polyamine is N,N,N',N'-Tetramethyl-1, 3-propanediamine, Structure 3 wherein each $R_1$ and $R_2$ are independently selected from H and $CH_3$, Structure 4 wherein each of $R_1$-$R_3$ is independently selected from H and $CH_3$, Structure 5 wherein each of $R_1$-$R_4$ is independently selected from H and $CH_3$, Structure 6, wherein each of $R_1$-$R_6$ is independently selected from H and $CH_3$, Structure 7 wherein each of $R_1$-$R_6$ is independently H or $CH_3$, or Structure 8 wherein each of $R_1$-$R_7$ is independently H or $CH_3$, provided that, when the cartridge or capillary is a capillary and the gel is of polyethylene oxide ("PEO"), the capillary is coated.

14. The cartridge or capillary of claim 13, wherein said at least one polyamine is of Structure 4 and is 1,4,7-Trimethyl-1,4,7-triazacyclononane.

15. The cartridge or capillary of claim 13, wherein said at least one polyamine is of Structure 1 and is 1, 2-Ethanediamine, N1-(2-aminoethyl) or 1, 2-Ethanediamine, N1-[2-(dimethylamino) ethyl]-N1, N2, N2-trimethyl-.

16. The cartridge or capillary of claim 13, wherein said at least one polyamine is N,N,N',N'',N''-Pentamethyldiethylenetriamine.

17. The cartridge or capillary of claim 13, wherein said gel further comprises polyethylene oxide.

18. The cartridge or capillary of claim 13, wherein said cartridge or capillary is a cartridge.

19. A composition for capillary electrophoretic separation of labeled glycans, said composition comprising a gel suitable for capillary gel electrophoresis of labeled glycans, which gel comprises at least one polyamine of any of the following structures:

Structure 1 wherein each of $R_1$-$R_3$ are independently selected from H and $CH_3$, Structure 3 wherein each $R_1$ and $R_2$ are independently selected from H and $CH_3$, Structure 4 wherein each of $R_1$-$R_3$ is independently selected from H and $CH_3$, Structure 5 wherein each of $R_1$-$R_4$ is independently selected from H or $CH_3$,

Structure 6,

Structure 6 wherein each of $R_1$-$R_6$ can independently be H or $CH_3$,
Structure 7

Structure 7 wherein each of $R_1$-$R_6$ is independently H or $CH_3$, or
Structure 8

Structure 8 wherein each of $R_1$-$R_7$ is independently H or $CH_3$, provided that, when the capillary electrophoretic separation takes place in a capillary containing the gel and the gel is of polyethylene oxide ("PEO"), the capillary is coated.

20. A cartridge or capillary loaded with a gel for capillary electrophoretic separation of labeled glycans, which gel comprises at least one polyamine of any of the following structures:

Structure 1

Structure 1 wherein each of $R_1$-$R_3$ are independently selected from H and $CH_3$,

Structure 3

Structure 3 wherein each $R_1$ and $R_2$ are independently selected from H and $CH_3$,

Structure 4

Structure 4 wherein each of $R_1$-$R_3$ is independently selected from H and $CH_3$,

Structure 5

Structure 5 wherein each of $R_1$-$R_4$ is independently selected from H and $CH_3$,

Structure 6,

Structure 6 wherein each of $R_1$-$R_6$ is independently selected from H and $CH_3$, Structure 7 wherein each of $R_1$-$R_6$ is independently H or $CH_3$, or

Structure 8 wherein each of $R_1$-$R_7$ is independently H or $CH_3$, provided that, when the cartridge or capillary is a capillary and the gel is of polyethylene oxide ("PEO"), the capillary is coated.

* * * * *